United States Patent [19]

Cohen

[11] Patent Number: 5,223,392
[45] Date of Patent: Jun. 29, 1993

[54] MONOCLONAL ANTIBODIES AGAINST GLYCATED ALBUMIN, HYBRID CELL LINES PRODUCING THESE ANTIBODIES, AND USE THEREFORE

[75] Inventor: Margo P. Cohen, New York, N.Y.

[73] Assignee: Exocell, Inc., Philadelphia, Pa.

[21] Appl. No.: 147,363

[22] Filed: Jan. 25, 1988

[51] Int. Cl.$^5$ .............. G01N 33/53; C12N 5/12; C07K 15/14

[52] U.S. Cl. .............. 435/7.1; 435/7.9; 435/172.2; 435/240.27; 436/501; 436/548; 436/88; 530/388.25

[58] Field of Search .......... 435/172.2, 240.27, 7.1, 435/7.9; 424/85; 436/501, 548, 88; 530/387, 388.25; 935/110

[56] References Cited

U.S. PATENT DOCUMENTS 4,629,692 12/1986 Dean .................... 435/7
4,797,473 1/1989 Tarsio et al. ............ 530/387

FOREIGN PATENT DOCUMENTS 0230934 8/1987 European Pat. Off. .
0257421 2/1988 European Pat. Off. .

OTHER PUBLICATIONS

Cohen et al., "Production and Characterization of Monoclonal Antibodies Against Human Glycoalbumin", J. Immunol. Meth. (1989), 117:121–129.
Curtiss, J. Clin. Invest., vol. 72, pp. 1427–1438, 1983.
Johnson, Clinical Chimica Acta, vol. 127, pp. 87–95, 1982.
San–Jil, Clinical Chemistry, vol. 31, pp. 2005–2006, 1985.
Nakayama, J. Imm. Methods, vol. 99, pp. 95–100, 1987.

Primary Examiner—Esther L. Kepplinger
Assistant Examiner—Toni R. Scheiner
Attorney, Agent, or Firm—Banner, Birch, McKie & Beckett

[57] ABSTRACT

The present invention is directed to monoclonal antibodies, and hybridomas which produce them, which are preferentially reactive with glycated albumin and insignificantly reactive with other proteins, as well methods of using these monoclonal antibodies to detect glycated albumin.

13 Claims, No Drawings

MONOCLONAL ANTIBODIES AGAINST GLYCATED ALBUMIN, HYBRID CELL LINES PRODUCING THESE ANTIBODIES, AND USE THEREFORE

BACKGROUND OF THE INVENTION

This invention is directed to monoclonal antibodies against glycated albumin, hybrid cell lines producing these antibodies, and methods of using these monoclonal antibodies.

DESCRIPTION OF THE BACKGROUND ART

Periodic assessment of the prevailing blood glucose level is essential to establishing and maintaining control of diabetes mellitus. The mainstay of monitoring diabetes control is measurement of the blood glucose concentration and of the extent to which certain circulating proteins have become nonenzymatically glycated. The major proteins for which it is has found useful to measure the amount of nonenzymatic glycation are hemoglobin and albumin.

Glycated albumin is formed in the body from a reaction between glucose and albumin which is the principal protein in serum. The primary factor which influences the amount of albumin that becomes glycated is the concentration of glucose in the blood. Thus, when blood sugar is elevated, as it is in diabetic people whose diabetes is not well controlled, high levels of glycated albumin are present. Because the reaction is slow and continuous, the absolute amount of glycated albumin in a person's blood reflects the average blood glucose concentration to which albumin has been exposed during its life in the circulation. This period is about 2 weeks. A single glycated albumin determination therefore provides a window for monitoring overall diabetic control during the preceding 10-20 days. An elevated glycated albumin level tells the physician and the patient that changes in the antidiabetic regimen must be made. Conversely, a decline in a previously elevated glycated albumin indicates that a response to the changes in the therapeutic regimen that were instituted 1-3 weeks earlier is occurring.

Because there is convincing evidence that poor glucose control is a major factor in causing diabetic complications such as blindness and kidney failure, achieving and maintaining normal blood glucose levels in diabetic people is not a philosophical but an ethical issue. Modern medicine dictates that every effort be made to nomalize blood sugar throughout each 24 hour period. This can be accomplished with oral agents, insulin injections, continuous insulin delivery systems, or pancreatic or inlet cell transplants. The therapeutic success of any of these regimens is assessed by periodic measurement of blood glucose and circulating glycated protein. Glycated hemoglobin is measured in the form of $HbA_{1c}$ by ion exchange of high pressure liquid chromatography. Hemoglobin glycated in the $A_{1c}$ configuration as well as at other sites along the peptide chain is designated total glycated hemoglobin and is measured by affinity chromatography.

Blood glocose is measured 1-4 times per day using a technique known as home glucose monitoring. In performing this test the patient pricks his finger with a disposable lancet, and applies the resultant drop of blood to a chemically impregnated strip that changes color according to the amount of glucose in the blood sample. The color indicates what the level of blood sugar is at the moment that it is measured. Glycated hemoglobin or $HBA_{1c}$ is generally measured once every 3 months to determine whether such momentary and random blood glucose values represent the long-term integrated level of diabetic control over many weeks to months. Glycated albumin can be measured at 1 to 2 week intervals to determine more recent overall control, and to detect and document improvement or deterioration in control of more recent temporal relevance.

Methods described to measure glycated albumin and other serum proteins include a colorimetric procedure based on reaction with thiobarbituric acid, affinity chromatography, high pressure liquid chromatography to measure furosine, and the fructosamine assay. Many of these tests have drawbacks relating to reproducibility, cost, expensive instrumentation, accuracy or other factors.

For example, the fructosamine assay, which relies on the generation of a colored product upon reaction of N-substituted ketoamine (fructosamine) with nitroblue tetrazolium and which can be adapted for automatic analyzers, was expected to overcome some of these drawbacks (Johnson, et al, *Clin. Chim. Acta* 127:87, 1982; San-Gil, et al, *Clin Chim*, 31:2005-6, 1985). However, this assay depends on a nonspecific reducing activity and measures not only glycated albumin, but all glycated serum proteins. As a consequence, it is difficult to interpret what is being measured and what retrospective period of time relating to glycemic status the determination reflects. This is because there is great variation on the reactivity of individual serum proteins with glucose, as well as in their residence times in the circulation. Therefore, each protein may have been exposed to a hyperglycemic milieu for a different interval, and each may have been glycated to a different extent. Proteins with a longer half-life undergo more extensive glycation and thereby raise the amount of fructosamine disproportionate to their relative concentration in serum, giving an imprecise estimate of the period during which diabetic control improved or deteriorated. Further, situations in which serum proteins are increased or decreased yield spuriously elevated or low values in the fructosamine assay.

It therefore would be desirable to accurately and specifically quantity the amount of circulating glycated albumin, a protein with a defined residence time in the circulation, since its measurement provides a precise index of the prevailing blood glucose concentrations during the preceding 10 to 20 days.

SUMMARY OF THE INVENTION

It is an object of the present invention to provide a monoclonal antibody that is capable of reacting with glycated albumin for purposes of effective diagnosis of disease.

It is another object of the present invention to provide methods for the diagnosis of disease using monoclonal antibodies which react with glycated albumin, but not other proteins.

The present invention thus relates to monoclonal antibodies reactive with an epitope present on glycated albumin but which are insignificantly reactive with other proteins, whether glycated or unglycated. The invention further includes hybrid cell lines which produce these antibodies, as well as methods of using and processes of preparing these monoclonal antibodies.

It is an object of the present invention to provide a novel and improved method for measurement of nonenzymatically glycated albumin.

Another object of the invention is to provide a novel and improved method for monitoring glycemic control in patients with diabetes by measuring the amount of glycated albumin in their blood.

Another object of the invention is to provide a novel method for making the diagnosis of diabetes with a single blood test.

Another object of the invention is to provide a novel method for confirming the diagnosis of diabetes when results from the oral glucose tolerance test are equivocal.

These and other objects of the invention are achieved by using a monoclonal antibody that specifically recognizes glycated residues of albumin. The epitope for this monoclonal antibody is in the ketoamine construct, which is the form in which the epitope occurs in vivo such that there has been no artificial modification as, for example, borohydride reduction. This differs from the sites recognized by other antibodies against glycated proteins described in the art, in which the glycated epitope has been converted to glucitol-lysine by borohydride reduction (Curtiss and Witztum, *J. Clin. Invest.*, 72:1427–1438, 1983; Nakayama et al., *J. Immunolog. Methods*, 99:95–100, 1987).

DETAILED DESCRIPTION

The present invention relates to monoclonal antibodies to glycated albumin. These monoclonal antibodies are highly useful for immunological detection of glycated albumin associated with certain diseases as, for example, diabetes mellitus.

The present invention is based on the principle of specific immunologic recognition and reaction between a monoclonal antibody and the antigenic epitope to which the antibody uniquely and specifically binds. The recognition and binding can be detected, for example, by an ELISA type test, wherein the antibody is immobilized on a solid phase support, such as the bottom of a plastic well. Test fluid and enzyme labeled reagent and enzyme substrate are reacted with the immobilized antibody through a number of dilution, incubation and washing steps, and bound and free reagents are separated. A color forming reaction takes place as a result of binding of the antigen to antibody and the consequent reaction of the enzyme upon its substrate. The formation of color indicates the presence of glycated albumin in the test sample, and the intensity of the color provides a quantitative measure of the amount of glycated albumin in the sample. The ELISA type assay may also be performed by immobilizing enzyme-linked monoclonal antibody and adding test fluid and substrate, and by immobilizing antigen or sample and adding monoclonal antibody, enzyme labeled reagent and substrate.

Nonenzymatic glycation proceeds through the formation of a Schiff base between the carbonyl group of glucose (C1) and a free amino group of an amino acid. Basically, only two types of free amino groups are present, mainly, at the N-terminus of the protein and the epsilon amino groups of lysine or hydroxylysine. The resulting aldimine linkage which is formed is stabilized by undergoing Amadori rearrangement to form a ketoamine with the carbonyl at C2. Thus, the stable product is N-1-(1-deoxyfructosyl) lysine (Bunn, et al., *Journal of Biological Chemistry*, 254:3892–3898, 1979; Bunn, et al., *Science*, 200:21–27, 1978).

In non-diabetics the principal site on albumin which undergoes in vivo glycation is at lysine-525. It is this position which accounts for about 33% the overall glycation. However, glycation occurs at other sites, including lysine-199, lysine-281 and lysine-439 (Garlick, et al., *Journal of Biological Chemistry*, 258:6142–6146, 1983; Fluckiger, *Monographs in Atherosclerosis*, 13:53–62, 1985; Iberg, et al., *Journal of Biological Chemistry*, 261:13542–13545, 1986). The reactivity of these other sites with glucose is greater in in vitro systems than in in vivo systems and it may be greater in diabetic than in non-diabetic subjects. From this it appears that the lys-lys sequence, as is present at the lys-525 site, is the site most reactive with glucose, followed by lys-his and lys-his-lys.

The monoclonal antibody of the present invention A717, was raised in mice which had been immunized with native (in vivo) glycated albumin and reacts even better with synthetic (in vitro) glycated albumin than with native glycated albumin. This suggests that the antibody recognizes epsilon-D-fructose-lysine whether it resides in sequence with another lysine or a histidine. The recognition of glycated polylysine by A717 (Example 6) supports this explanation. However, it is clear that there are steric or conformational components specific to albumin in the epitopic recognition since A717 does not recognize epsilon-D-fructose-lysine in unrelated proteins and A717 is less reactive with equivalent amounts of glycated polylysine than it is with either native or synthetic glycated albumin.

Authentic glycated albumin (antigen) is prepared by subjecting normal or diabetic plasma first to chromatography on Affi-gel blue (Day, et al, *J Biol Chem*, 254:9394–9400, 1979; Travis, et al, *Biochem J*, 157:301–306, 1976) to separate albumin from other plasma proteins, and then subjecting the material that elutes with 2M sodium chloride to affinity chromatography on phenylboronate agarose (Brownlee, et al, *Diabetes* 29:1044–1047, 1980; Rendell, et al, *J Lab Clin Med*, 105:63–69, 1985; Wiley, et al, *Diabetologia*, 27:56–58, 1984) to isolate the glycated albumin from the nonglycated form. This isolate is designated native in vivo glycated albumin.

Glycated albumin can also be prepared by incubating authentic native human albumin for 7 days at 25° C. in a solution containing 500 mg/dl of glucose buffered in PBS to pH 7.4. The preparation is dialyzed to remove free glucose, and subjected to affinity chromatography on phenylboronate to separate unreacted albumin from the glycated albumin. This isolate is designated synthetic in vitro glycated albumin.

The general method used for production of hybridomas secreting monoclonal antibodies is well known to those of ordinary skill in the art. Illustrative of the techniques utilized in the present invention are those described in *Proceedings of the National Academy of Science, USA*, 75: 3405, (1978).

In brief, female BALB/c mice were immunized over a four week period with glycated albumin. After the final immunization, the animals were sacrificed and spleen cells fused with a mouse non-secretor myeloma cell line. Hybridomas were screened for antibody production and positive clones were tested for monoclonal antibody binding to glycated albumin.

The isolation of other hybridomas secreting monoclonal antibodies with the specificity of the monoclonal antibodies of the invention can be accomplished by one of ordinary skill in the art by producing anti-idiotypic antibodies (Herlyn, et al., *Science*, 232:100, 1986) which can be used for screening. An anti-idiotypic antibody is an antibody which recognizes unique determinants present on the monoclonal antibody produced by the hybridoma of interest. These determinants are located in the hypervariable region of the antibody. It is this region which binds to a given epitope and, thus, is responsible for the specificity of the antibody. The anti-idiotypic antibody can be prepared by immunizing an animal with the monoclonal antibody of interest. The animal immunized will recognize and respond to the idiotypic determinants of the immunizing antibody by producing an antibody to these idiotypic determinants. By using the anti-idiotypic antibodies of the second animal, which are specific for the monoclonal antibodies produced by a single hybridoma which was used to immunize the second animal, it is now possible to identify other clones with the same idiotype as the antibody of the hybridoma used for immunization and thereby greatly simplify and reduce the amount of screening needed to find other hybridomas secreting monoclonal antibodies with the specificity of the monoclonal antibodies of the invention.

Idiotypic identity between monoclonal antibodies of two hybridomas demonstrates that the two monoclonal antibodies are the same with respect to their recognition of the same epitopic determinant. Thus, by using anti-idiotypic antibodies to the epitopic determinants on a monoclonal antibody it is possible to identify other hybridomas expressing monoclonal antibodies of the same epitopic specificity.

Alternatively, it is possible to evaluate, without undue experimentation, a monoclonal antibody to determine whether it has the same specificity as the monoclonal antibody of the invention by determining whether the monoclonal antibody being tested prevents the monoclonal antibody of the invention from binding to a particular antigen with which the monoclonal antibody of the invention is normally reactive. If the monoclonal antibody being tested competes with the monoclonal antibody of the invention, as shown by a decrease in binding by the monoclonal antibody of the invention, then it is considered that the two monoclonal antibodies bind to the same epitope. Also, a monoclonal antibody can be tested for the same reactivity pattern for glycated albumin as the monoclonal antibody of the invention.

Under certain circumstances, monoclonal antibodies of one isotype might be more preferable than those of another in terms of their diagnostic efficacy. Particular isotypes of a monoclonal antibody can be prepared either directly, by selecting from the initial fusion, or prepared secondarily, from a parental hybridoma secreting monoclonal antibody of different isotype by using the sib selection technique to isolate class-switch variants (Steplewski, et al., *Proceedings of National Academy of Science*, USA, 82: 8653, 1985; Spira, et al., *Journal of Immunological Methods*, 74: 307, 1984). Thus, the monoclonal antibodies of the invention would include class-switch variants having the specificity of monoclonal antibody A717 which is produced by ATCC HB 9596.

The term "antibody" as used in this invention is meant to include intact molecules as well as fragments thereof, such as, for example, Fab and F(ab')$_2$, which are capable of binding the epitopic determinant.

The monoclonal antibodies of the invention are particularly suited for use in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Regardless of the type of immunoassay which is used, the concentration of antibody utilized can be readily determined by one of skill in the art.

The monoclonal antibodies of the invention can be bound to many different carriers and used to detect the presence of glycated albumin antigen. Examples of well-known carriers include glass, polystyrene, polyvinyl chloride, polypropylene, polyethylene, polycarbonate, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibody, or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds. Those of ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

For purposes of the invention, the glycated albumin which is detected by the monoclonal antibodies of the invention may be present in various biological fluids and tissues. Any sample containing a detectable amount of glycated albumin can be used. Normally, a sample is a liquid such as urine, saliva, cerebrospinal fluid, blood, serum and the like, or a solid or semi-solid such as tissue, feces and the like.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific anti-hapten antibodies.

As used in this invention, the term "epitope" is meant to include any determinant capable of specific interaction with the monoclonal antibodies of the invention. Epitopic determinants usually consist of chemically active surface groupings of molecules such as amino acids or sugar side chains and usually have specific three dimensional structural characteristics, as well as specific charge characteristics.

The term "diagnostically effective" means that the amount of monoclonal antibody is in sufficient quantity to enable detection of glycated albumin having the epitope for which the monoclonal antibodies of the invention are specific.

The term "preferentially reactive" means that the monoclonal antibodies of the invention can distinguish between glycated albumin and other proteins, whether or not these other proteins are glycated. Especially significant is the ability of the monoclonal antibodies of the invention to distinguish between glycated albumin and unglycated alblumin. The term "insignificantly reactive" means that the degree of reactivity seen between the monoclonal antibody of the invention and other glycated protein does not hinder the diagnostic or usefulness of the monoclonal antibody. For example, when used diagnostically the monoclonal antibodies of the invention bind so much more significantly to glycated albumin as compared to other glycated proteins that the presence of glycated albumin in a sample is clearly distinguishable from any background due to binding of the antibodies to other glycated proteins.

Monoclonal antibody A717 can be utilized in the present invention. A717 is obtained from, or has the identifying characteristics of, an antibody obtained from the cell line having ATCC accession number HB 9596. This cell line was placed on deposit for 30 years at the American Type Culture Collection (ATCC) in Rockville, Md. prior to Dec. 2, 1987.

The above disclosure generally describes the present invention. A more complete understanding can be obtained by reference to the following specific examples which are provided herein for purposes of illustration only, and are not intended to limit the scope of the invention.

EXAMPLE 1

Preparation of Hybridoma Cell Lines Producing Monoclonal Antibodies to Glycated Albumin Female BALB/c mice were immunized with 100 ug of in vivo or in vitro glycated albumin dissolved in phosphate buffered saline (PBS) consisting of 0.8% NaCl, 0.02% KCl, 0.008M $Na_2HPO_4$ and 0.0015M $KH_2PO_4$ (pH 7.4) and mixed with Freund's complete adjuvant. The mixture (1:1) was injected intraperitoneally. Seven days later, the mice were injected with antigen mixed with incomplete adjuvant (1:1), with antigen alone one week later, and then on three sequential days during the fourth week. On the day after the last injection the animals were sacrificed and the spleens removed. The spleen cells were fused with SP 2/0 myeloma cells and hybridoma colonies established according to standard techniques (Kennet, R. H., McKearn, T. J. and Bechtol, K. B. [eds]: *Monoclonal Antibodies; Hybridomas: A New Dimension in Biological Analyses*, Plenum Press, New York and London, 1982). The resulting colonies with binding activity to in vivo or in vitro glycated albumin were cloned twice by limiting dilution.

EXAMPLE 2

Characterization of Monoclonal Antibodies Reactive with Glycated Albumin

Duplicate individual samples of human albumin, in vivo glycated albumin, and in vitro glycated albumin (20-50 ug each) were subjected to SDS-polyacrylamide slab gel electrophoresis according to standard techniques (Laemmli, *Nature*, 227:680, 1970). One of each duplicate set of gels was stained for protein to determine the electrophoretic migration position of the native and glycated albumins. The other gel of each duplicate set was transferred electroporetically to nitrocellulose, blocked by soaking in a solution of 1% gelatin in 0.1M Tris (pH 8.0) in PBS for 1 hour and soaked for 2 hours in a solution of monoclonal antibody A717 (10 ml per lane of hybridoma culture supernatant) raised against in vivo glycated albumin. After washing, the nitrocellulose strips were then soaked in a 0.1% solution of horseradish peroxidase-conjugated goat anti-mouse IgG antibody (Bio-Rad, Richmond, CA), followed after extensive washes with Tris/PBS and detergent (0.05% Tween 20) by a 0.03% solution of hydrogen peroxide and color developer containing 4-chloronaphthol. Electrophoretic transfer and immunoblotting were performed according to standard techniques (Tobin, et al, *Proc Natl Acad of Sci*, 76:4350-4354, 1979). The nitrocellulose strips were examined for the presence and position of colored protein bands, which indicate the binding of the monoclonal antibody to the antigen that it recognizes.

Native albumin migrated to a position in the polyacrylamide gel corresponding to a molecular weight of 60,000, as expected. The electrophoretic mobility of the glycated albumins was slightly greater, compatible with minor modification of charge as a result of nonenzymatic glycation of the free amino group of lysine residues.

Monoclonal antibody A717 did not bind to native albumin as evidenced by the fact that no colored band could be visualized after electrophoretic transfer of this protein and its exposure to monoclonal antibody A717, enzyme labeled reagent, and substrate. In contrast, monoclonal antibody A717 specifically bound to in vivo glycated albumin, as shown by the fact that a single colored band corresponding to the electrophoretic migration position of this antigen was visualized after its exposure to monoclonal antibody A717 and enzyme labeled reagent and substrate.

Monoclonal antibody A717 recognized and bound to in vitro glycated albumin, given that a single colored band corresponding to the electrophoretic migration position of this antigen was visualized after its reaction with monoclonal antibody A717 and enzyme labeled reagent and substrate. In addition, it was determined by gel diffusion that A717 has isotype $IgG_1$.

As shown in these studies, monoclonal antibody A717 specifically recognizes and binds to glycated albumin, but not native (unglycated) albumin. The recognition of and binding to glycated albumin by monoclonal antibody A717 is specific for ketoamine groups, since the antibody reacts with in vitro as well as in vivo glycated albumin and both of these are glycated in the ketoamine construct.

EXAMPLE 3

Detection of Glycated Albumin in Human Plasma Using Monoclonal Antibody A717

Samples of human plasma were electrophoresed on SDS-polyacrylamide gels and electrophoretically transferred to nitrocellulose and immunoblotted according to methods in Example 2.

Human plasma yielded multiple protein bands, as expected with standard protein staining, ranging in molecular weight from less than 20,000 to over 200,000. In contrast, only one band was visualized after electrophoretic transfer and reaction with monoclonal antibody A717 and enzyme labeled reagent and substrate.

The location of this band, which represents the colored product formed upon reaction of the unique monoclonal antibody-antigen complex, coincides with that of authentic in vivo glycated albumin. Thus, monoclonal antibody A717 can specifically recognize and bind to glycated albumin in human plasma which contains a multiplicity of proteins, some of which exist in glycated forms. Monoclonal antibody A717 does not recognize or bind to glycated proteins aside from albumin.

EXAMPLE 4

Relative Reactivity of A717 for Unglycated and Glycated Albumin 500 ng of native albumin, in vivo glycated albumin, or in vitro glycated albumin were immobilized onto plastic wells using carbonate-bicarbonate coupling buffer (pH 9.6) for 18 hours at 4° C. After washing to remove unbound antigen, followed by blocking for 30 minutes at room temperature with 1.0% gelatin/PBS/0.05% Tween 20, monoclonal antibody A717 (100 ul of hybridoma culture supernatant or from about 10 to about 100 ng of purified A717 in 0.1% gelatin), was added to each well and allowed to react for 2 hours. After washing with 0.1% Tween 20 in PBS, horseradish peroxidase-conjugated goat antimouse IgG antibody in 0.1% gelatin/PBS/Tween was added and incubated for 1 hour at room temperature. After extensive washes with PBS/Tween, the presence and intensity of colored product were determined using ortho-phenyldiamine (OPD) in phosphate-citrate buffer (pH 5.0) with 0.03% hydrogen peroxide and read using an ELISA reader at an absorbance of 450 mm.

TABLE 1

| ANTIGEN | COLOR REACTION |
|---|---|
| Albumin | — |
| in vivo glycated albumin | + + + |
| in vitro glycated albumin | + + + + |

As shown in TABLE 1, monoclonal antibody (A717) can selectively discriminate native unglycated albumin from in vivo and in vitro glycated forms of albumin in an ELISA type assay. Under these experimental conditions 100 ul of unpurified monoclonal antibody A717 was sensitive to 500 ng of antigen. In vitro glycated albumin in equal amount to in vivo glycated albumin gave more intense color because more of its lysine amino groups are glycated.

EXAMPLE 5

Sensitivity of Monoclonal Antibody A717 in Detecting Glycated Albumin in Human Plasma Method A 100 ul of human plasma from a nondiabetic donor containing an estimated 5% glycated albumin at dilutions of 1:1000, 1:10,000, 1:100,000 was immobilized onto plastic wells using coupling buffer as in Example 4. Monoclonal antibody A717 was purified using the BioRad (Richmond, CA) Protein A system. After washing with PBS/Tween and blocking with 1% gelatin in PBS/Tween for 1 hour at room temperature, purified monoclonal antibody A717 (10–100 ng) was added to each well and allowed to react for 1 hour at room temperature. After washing with PBS/Tween, peroxidase conjugated goat antimouse IgG antibody at a 1:1000 dilution was added and allowed to incubate for 2 hours at 23° C. After this time, the plates were washed with PBS/0.05% Tween, OPD substrate was added, and the reaction allowed to proceed. The reaction was stopped after 10 minutes with 2M $H_2SO_4$ (50 ul) and the presence and intensity of colored product were determined as in Example 4.

TABLE 2

| PLASMA DILUTION | ABSORBANCE |
|---|---|
| 1:1000 | .32 |
| 1:10,000 | .23 |
| 1:100,000 | .05 |

Monoclonal antibody (A717) can selectively discriminate and quantitate glycated albumin in human serum. This selectivity and discrimination can be obtained without subjecting serum to any modifying or preparative steps or procedures.

Method B 100 ul of monoclonal antibody A717 (hybridoma culture supernatant) was immobilized onto plastic wells with coupling buffer as in Example 4. After washing with PBS/Tween, 100 ul of authentic in vivo or in vitro glycated albumin or plasma estimated to contain equivalent amounts of glycated albumin, as determined by the reaction of thiobarbituric acid with 5-hydroxy-methylfurfuraldehyde to measure glucose in ketoamine linkage (Cohen, *Diabetes and Protein Glycosylation*, p. 18, Springer-Verlag, New York, 1986), was added as a 60% solution in 0.1% gelatin and allowed to react for 1 hour at room temperature. After washing with PBS/Tween, peroxidase conjugated goat anti-human albumin antibody at 1:200 dilution in 0.1% gelatin was added, and the reaction allowed to proceed. After washing, reactivity was determined by measuring the presence and intensity of colored product were determined as in Example 4.

TABLE 3

| ANTIGEN | ANTIGEN CONCENTRATION[a] | ABSORBANCE |
|---|---|---|
| Albumin | 1.0 | — |
| in vivo Glycated Albumin | 1.0 | 1.10 |
|  | 0.5 | 0.66 |
|  | 0.1 | 0.25 |
| in vitro Glycated Albumin | 1.0 | 1.51 |
|  | 0.5 | 0.98 |
|  | 0.1 | 0.41 |
| DILUTED |  |  |
| Plasma 1:200 | 1.0[b] | 0.953 |
| 1:1000 | 0.2[b] | 0.523 |
| 1:2000 | 0.1[b] | 0.096 |

[a] ug
[b] estimated glycated albumin

This data shows that monoclonal antibody A717 can specifically detect and quantitate both in vivo and in vitro glycated albumin in pure form and in vivo glycated albumin in human plasma.

EXAMPLE 6

Reactivity of Monoclonal Antibody A717 With Various Glycated Proteins

Glycation of various related and unrelated proteins and peptides was accomplished by incubating the authentic protein for 7 days at 25° C. in a solution containing 500 mg/dl of glucose buffered in PBS to pH 7.4. The preparations were dialyzed to remove free glucose and then subjected to affinity chromatography on phenylboronate to separate unreacted from reacted (glycated) protein.

500 ng (0.5 ug) of the glycated proteins or peptides identified below were immobilized on plastic wells as described in Example 4. After washing with PBS/Tween and blocking with 1% gelatin as in Example 5, Method A, 100 ul of monoclonal antibody (100 ul hybridoma culture supernatant or 10–100 ng purified monoclonal antibody) was added to each well and allowed to react for two hours at 23° C. After washing and addition of horseradish peroxidase conjugated goat anti-mouse IgG and substrate, the presence and intensity of colored product were determined as in Example 4.

TABLE 4

| ANTIGEN | ABSORBANCE |
|---|---|
| in vitro glycated albumin | .600 |
| in vivo glycated albumin | .295 |
| albumin | — |
| in vitro glycated alpha-globulin | — |
| in vitro glycated beta-globulin | — |
| in vitro glycated gamma-globulin | — |
| in vitro glycated polylysine | .140 |

These results show that monoclonal antibody A717 does not recognize or bind to other proteins even when, as shown here with alpha, beta and gamma globulin, these proteins have epsilon-D-fructose lysine residues. The antibody recognizes glycated polylysine, thereby confirming that the antibody is site specific for epsilon-D-fructose lysine when it resides in albumin.

The invention now being fully described, it will be apparent to one of ordinary skill in the art that many changes and modifications can be made without departing from the spirit or scope of the invention.

I claim:

1. A continuous hybridoma cell line capable of secreting a monoclonal antibody which specifically binds an epitope which is found on native glycated albumin which has been subjected to no artificial modification but which is not found on unglycated albumin, said epitope occurring at both lys-lys and lys-his sequences, said antibody specifically binding more than one of said sequences located at a residue selected from the group consisting of lysine-199, lysine-281, lysine-439, and lysine-525, and said antibody being insignificantly reactive with other proteins.

2. The hybridoma of claim 1, wherein said proteins are glycated.

3. The hybridoma of claim 1, wherein said hybridoma is ATCC HB 9596 or a hybridoma capable of secreting isotype switch variants of the antibodies secreted by ATCC HB 9596.

4. A monoclonal antibody specifically binds the glycated albumin epitope specifically bound by the monoclonal antibody produced by cell line ATCC HB 9596.

5. The monoclonal antibody, according to claim 4, wherein said monoclonal antibody is produced by cell line ATCC HB 9596.

6. A method of quantitating glycated albumin which comprises:

contacting a sample suspected of containing glycated albumin with a diagnostically effective amount of a monoclonal antibody, or fragment thereof, said monoclonal antibody or fragment thereof specifically binds an epitope which is found on native glycated albumin which has been subjected to no artificial modification but which is not found on unglycated albumin, said epitope occurring at both lys-lys and lys-his sequences, said antibody specifically bound more than one of said sequences located at a residue selected from the group consisting of lysine-199, lysine-281, lysine-439, and lysine-525, and said antibody being insignificantly reactive with other proteins; and quantitating monoclonal antibody or fragment thereof bound to components of the sample, amounts of bound monoclonal antibody or fragment thereof correlating with amounts of glycated albumin in the sample.

7. The method of claim 6, wherein said proteins are glycated.

8. The method of claim 6, wherein said antibody is produced by cell line ATCC HB 9596.

9. The method of claim 6, wherein said monoclonal antibody is detectably labeled.

10. The method of claim 9, wherein said detectable label is selected from the group consisting of a radioisotope, a fluorescent compound, a colloidal metal, a chemiluminescent compound, a bioluminescent compound and an enzyme.

11. The method of claim 6, wherein said monoclonal antibody specifically binds the glycated albumin epitope specifically bound by the monoclonal antibody produced by cell line ATCC HB9596.

12. The hybridoma of claim 1, wherein said antibodies specifically bind the glycated albumin epitope specifically bound by the monoclonal antibody produced by cell line ATCC HB9596.

13. A monoclonal antibody which specifically binds an epitope which is found on native glycated albumin which has been subjected to no artificial modification but which is not found on unglycated albumin, said epitope occurring at both lys-lys and lys-his sequences, said antibody specifically binding more than one of said sequences located at a residue selected from the group consisting of lysine-199, lysine-281, lysine-439, and lysine-525, and said antibody being insignificantly reactive with other proteins.

* * * * *